United States Patent
Varney

[11] Patent Number: 5,822,801
[45] Date of Patent: Oct. 20, 1998

[54] FACE SHIELD

[76] Inventor: Marna L. Varney, 12 Bay Rd., Brookhaven Hamlet, N.Y. 11719

[21] Appl. No.: 883,783

[22] Filed: Jun. 27, 1997

[51] Int. Cl.$^6$ ........................................ A42B 1/18
[52] U.S. Cl. .......................... 2/206; 2/114; 2/9; 132/319
[58] Field of Search .................. 2/206, 174, 9, 2/15; 132/319, 320, 333; 359/838; D29/104–108, 100, 17; 15/160; D28/9, 10, 99

[56] References Cited

U.S. PATENT DOCUMENTS

| | | | |
|---|---|---|---|
| D. 192,904 | 5/1962 | Glastal | D28/9 |
| D. 210,183 | 2/1968 | Ross | D28/9 |
| D. 225,910 | 1/1973 | Kurianski | D28/9 |
| D. 354,585 | 1/1995 | Rudy | D28/9 |
| D. 370,303 | 5/1996 | Borstel | D28/9 |
| D. 377,405 | 1/1997 | Morell | D29/108 |
| 1,492,196 | 4/1924 | Berestrom | 132/333 |
| 3,328,806 | 7/1967 | Allegro | 2/9 |
| 3,488,772 | 1/1970 | Sturm | 132/333 |
| 3,602,913 | 9/1971 | Neese | 2/9 |
| 3,772,707 | 11/1973 | Alosi et al. | 2/174 |
| 3,963,034 | 6/1976 | Runberg et al. | 2/9 X |
| 4,396,027 | 8/1983 | Loewenstine | |
| 4,837,861 | 6/1989 | Cole | 2/9 |
| 5,311,888 | 5/1994 | Leigh | |

FOREIGN PATENT DOCUMENTS

| | | |
|---|---|---|
| 15849 | 7/1907 | United Kingdom . |
| 927453 | 5/1963 | United Kingdom . |
| 948667 | 2/1964 | United Kingdom . |

Primary Examiner—Gloria M. Hale
Attorney, Agent, or Firm—Collard & Roe, P.C.

[57] ABSTRACT

A face shield having a face portion made of a rigid transparent material and having a concave shape so as to conform to the shape of a face. A handle portion is integrally formed with the face portion and extends downward from the bottom of the face portion. The handle portion is hollow and has an open bottom end. A handle grip covers the handle portion and also has an open bottom end. A bottom plug is fit securely in the open bottom end of the handle grip. The bottom plug has an opening to allow air to pass through the handle portion and into the area of the face portion. A hook is provided on the bottom plug to allow the shield to be hung on a wall or other surface when not in use. The shield is used while applying sprayable hair products and keeps these products from contacting the face of the user.

7 Claims, 4 Drawing Sheets

FACE SHIELD

BACKGROUND OF THE INVENTION

1. Field of the Invention

This invention relates to a face shield. In particular, this invention relates to a portable, hand-held shield to protect the face when applying hair spray.

2. The Prior Art

The use of hair spray and other sprayable hair products is very popular among both men and women to assist in the styling of hair. Sprays are an effective way of evenly dispersing a small amount of hair styling product over the entire area of the head.

Unfortunately, the very reasons why hair styling sprays are so effective is also a cause of one of their major drawbacks: because the sprays disperse over a large area, some of the spray being used ends up on the user's face as well. This leads to a sticky feeling on the skin, as well as more serious consequences such as clogged pores, stinging eyes and inhalation of potentially hazardous chemicals present in some hair sprays.

Accordingly, there have been several attempts to provide face shields that keep sprayable hair products from contacting the skin and eyes. One such shield is shown in U.S. Pat. No. 4,837,861 to Cole, which discloses a molded plastic face shield having a reflective surface on the inside. A handle extends downward from the face portion for holding the shield in place.

Another type of face shield is shown in U.S. Pat. No. 4,396,027 to Loewenstine, which shows a flat, transparent face shield having an extending ear protector on one side. A handle extends downwardly from the face portion for holding the shield in place.

British Patent No. 948,667 shows another face shield, having an outwardly extending round face portion and a downwardly extending handle. Ventilation holes are provided in the face portion to allow the user to breathe comfortably.

While all of these devices serve to keep spray products away from the user's face to some extent, they all suffer from several drawbacks. First, it would be desirable to construct a face shield that conforms substantially to the contours of the human face, to protect all areas of the face from the spray. The flat type of face shield leaves a lot of open areas for the spray to penetrate. Second, it would be desirable to provide a way to ventilate the face shield to allow the user to breathe and prevent fogging, while keeping the face-covering portion completely transparent.

SUMMARY OF THE INVENTION

It is therefore an object of the present invention to provide a face shield for preventing the deposit of sprayable hair products onto the face that is contoured to the shape of a human face.

It is another object of the present invention to provide face shield that is completely transparent in the face area to allow the user to see their face and hair while spraying hair products.

It is yet another object of the present invention to provide a face shield that allows the user to breathe freely while it is in use and which also prevents fogging.

It is a further object of the present invention to provide a face shield that is simple and inexpensive to manufacture.

These and other objects of the present invention are accomplished by a face shield comprising a face portion made of a rigid transparent material and having a concave shape so as to conform to the shape of a face. A handle portion is integrally formed with the face portion and extends downward from the bottom of the face portion. The handle portion is hollow and has an open bottom end. A handle grip covers the handle portion and also has an open bottom end.

A bottom plug is fit securely in the open bottom end of the handle grip. The bottom plug is divided into two halves along a center diameter, with one half being open to allow air to pass through the handle portion and into the area of the face portion, and the other half being solid. This allows the user of the face shield to breathe freely while the face shield is covering the face. In addition, this free flow of air through the handle portion prevents the face shield from fogging due to the user's breath on the shield.

The bottom plug has a solid portion which can be attached to or integrally formed with a hook to allow the face shield to be hung on a wall or other surface when the face shield is not in use.

The entire shield is preferably constructed of lightweight plastic, with at least the face portion being transparent. This way, the user has a full view of his or her face and head while applying the spray. The shield can be easily cleaned of hair spray residue simply by rinsing it in warm water with a small amount of detergent.

BRIEF DESCRIPTION OF THE DRAWINGS

Other objects and features of the present invention will become apparent from the following detailed description considered in connection with the accompanying drawings. It is to be understood, however, that the drawings are designed as an illustration only and not as a definition of the limits of the invention.

In the drawings, wherein similar reference characters denote similar elements throughout the several views.

DETAILED DESCRIPTION OF THE PREFERRED EMBODIMENT

Figure 1:
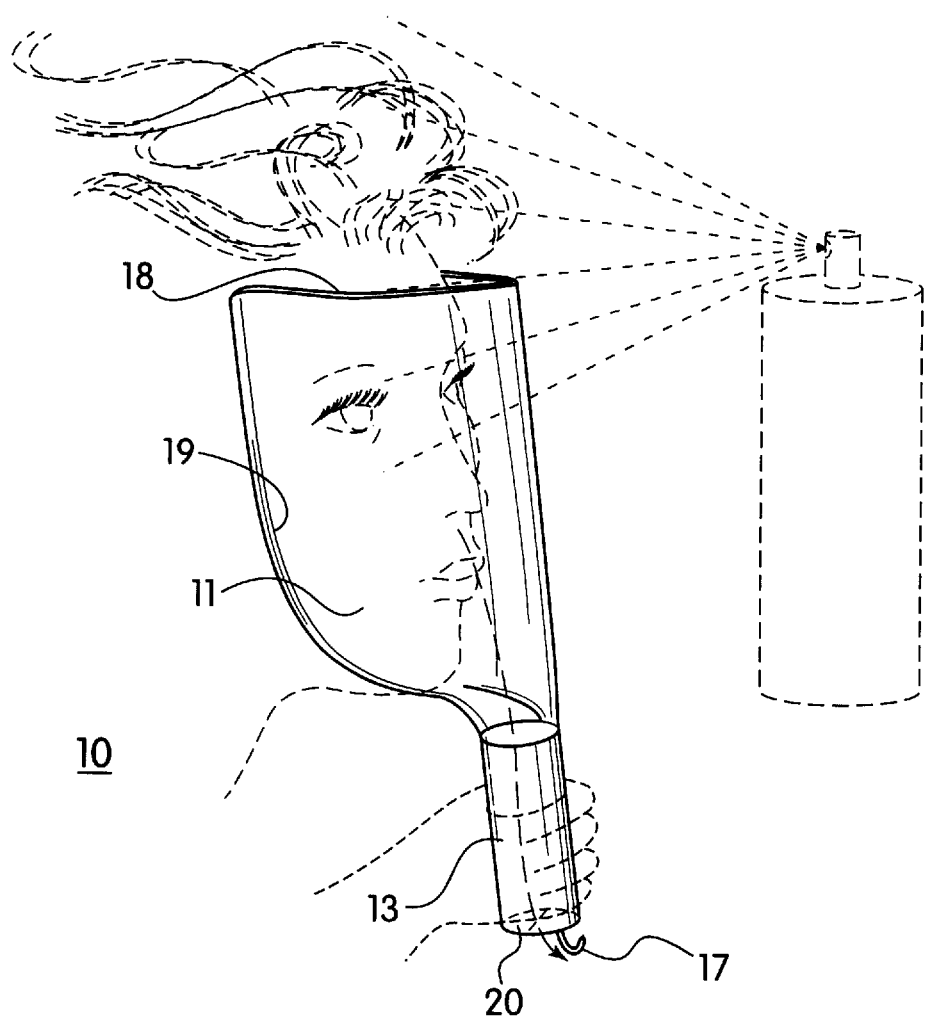
FIG. 1 is a perspective view of the face shield according to the invention.
Figure 2:
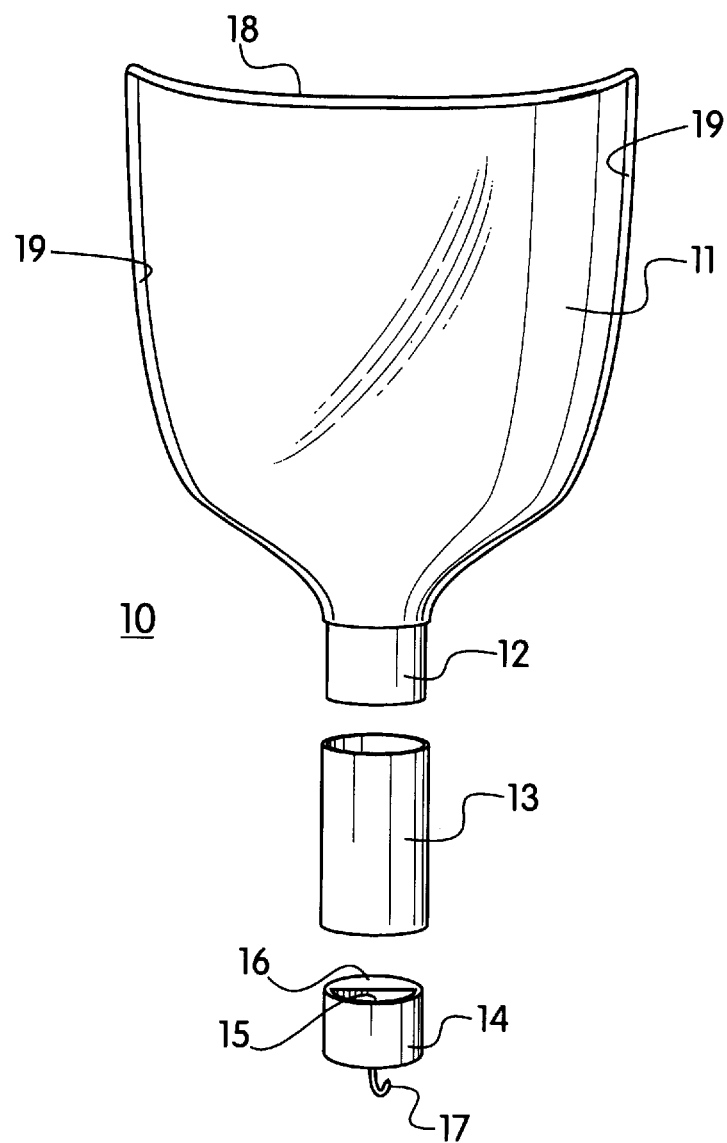
FIG. 2 is an exploded front view of the face shield according to the present invention.
Figure 3:
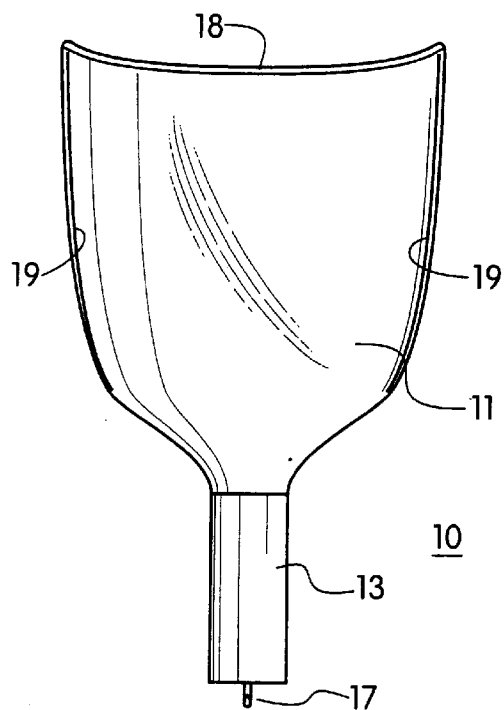
FIG. 3 is a rear view of the face shield according to the invention.
Figure 4:
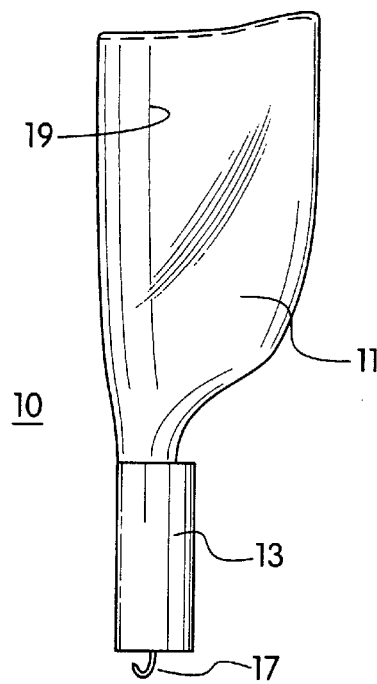
FIG. 4 is a left side view of the face shield according to the invention.
Figure 5:
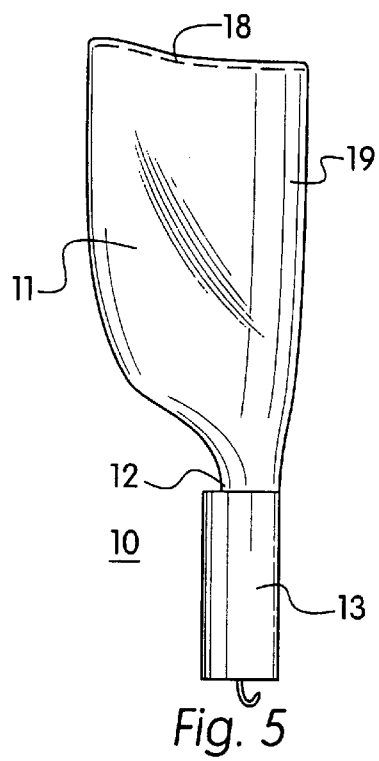
FIG. 5 is a right side view of the face shield according to the invention.
Figure 6:
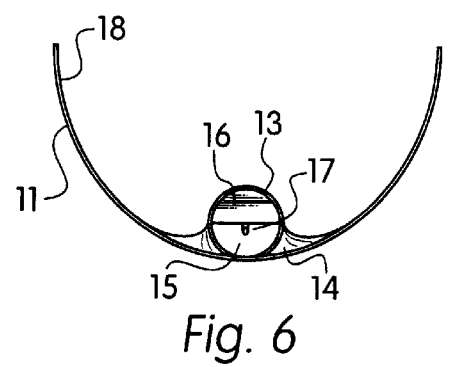
FIG. 6 is a top view of the face shield according to the invention.
Figure 7:
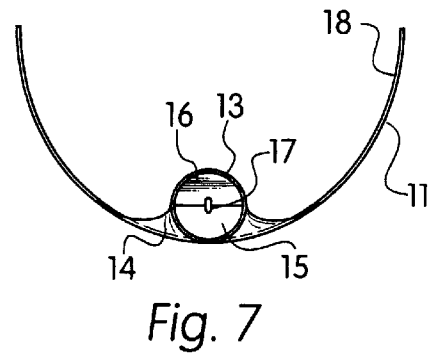
FIG. 7 is a bottom view of the face shield according to the invention.
Figure 8:
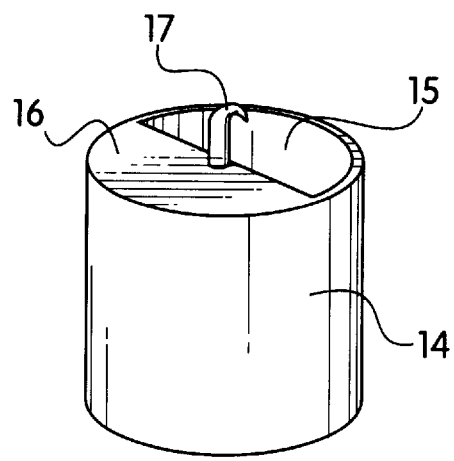
FIG. 8 is a side perspective view of the bottom plug of the face shield according to the invention.
Figure 9:
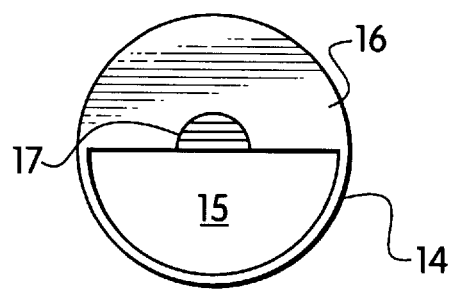
FIG. 9 is a bottom view of the bottom plug of the face shield according to the invention.

Referring now in detail to the drawings and, in particular, FIGS. 1–5, there is shown the face shield 10 according to the invention. Face shield 10 has face portion 11, connected to handle 12, which is covered by handle grip 13. Face portion 11 is concave in shape so that is covers the major portion of a user's face, from one ear to the other and from the top of the forehead to below the chin. Face portion 11 is integrally formed with handle 12, which is hollow, cylindrical in shape, and has an open bottom end 20.

Handle grip 13 is also cylindrical in shape and hollow with an open bottom end. Handle grip 13 is adapted to slide over handle 12 and allows the user to easily hold shield 10. Handle grip 13 is preferably made of an opaque, rigid material and may be optionally provided with a textured or coated surface to enhance the user's ability to grip the handle. Handle grip 13 may also be tinted a variety of colors to enhance the appearance of shield 10's.

A bottom plug 14 is placed securely into the open bottom end of handle grip 13, so that is slightly recessed in handle grip 13. As shown in FIGS. 6–9, bottom plug 14 is comprised of two halves, an open half 15 and a solid half 16. Open half 15 allows for the passage of air through handle 12 and into face portion 11 so that the user can breathe freely while shield 10 is covering the face.

A hook 17 is connected to solid half 16 to enable the hanging of shield 10 on a wall or other surface when not in use. Bottom plug 14 is preferably constructed of a resilient plastic or rubber, so that it can fit securely within handle grip 13, but can be removed with sufficient force if necessary.

In use, shield 10 is placed over the user's face so that face portion 11 covers a major portion of the user's face, as shown in FIG. 1. Shield 10 is held in place by the user's hand around handle grip 13. The user can then apply sprayable hair products to his or her hair using the other hand. When the spraying is completed and all residue has dispersed, the user removes shield 10 from his or her face. Shield 10 effectively prevents any of the hair products from being inhaled or contacting the user's face or eyes. During use, the user can breathe freely, because air can pass through plug 14, handle grip 13 and handle 12 into face portion 11. This free passage of air also keeps face portion 11 from fogging and obscuring the user's view during use.

In the drawings, shield 10 is also provided with a rim or lip 18 on the inside top edge of the shield, directed toward the user's face to provide an additional shielding affect to the upper forehead of the user's face. Rim 18 thus prevents spray chemicals from infiltrating the lower area of the user's face. Reinforcing ribs 19 are also provided adjacent to each side edge of shield 10 to add strength to the plastic material of the shield, so that a thinner, less expensive material can be used while still maintaining the structural integrity of the unit.

Accordingly, while only several embodiments of the present invention have been shown and described, it is obvious that many changes and modifications may be made thereunto without departing from the spirit and scope of the invention.

What is claimed is:

1. A face shield comprising:

a face portion made of a rigid transparent material, said face portion having a concave shape so as to conform to the shape of a face, and having two side edges, a bottom and a top edge;

a handle portion integrally formed with said face portion and extending downward from the bottom of said face portion, said handle portion being hollow and having an open bottom end;

a handle grip surrounding said handle portion and having an open bottom end; and a bottom plug having a bottom surface and adapted to fit securely in said open bottom end of said handle grip, said bottom plug being divided into two halves along a center diameter, one half being solid and one half having an opening to allow air to pass through the bottom plug and the handle portion and into the area of the face portion.

2. The face shield according to claim 1, further comprising a hook connected to the bottom surface of the bottom plug to allow the face shield to be hung on a wall or other surface.

3. The face shield of claim 1, additionally comprising a rim integrally formed along said top edge and directed inwardly toward the face of the user.

4. The face shield of claim 1, additionally comprising at least one reinforcing rib integrally formed adjacent to each of said side edges for adding strength to the rigid transparent material.

5. A face shield comprising:

a face portion made of rigid transparent material, said face portion having a concave shape so as to conform to the shape of a face, and having two side edges, a bottom and a top edge;

at least one reinforcing rib integrally formed adjacent to each of said side edges for adding strength to the rigid transparent material;

a handle portion integrally formed with said face portion and extending downward from the bottom of said face portion, said handle portion being hollow and having an open bottom end;

a handle grip surrounding said handle portion and having an open bottom end; and a bottom plug having a bottom surface and adapted to fit securely in said open bottom end of said handle grip, said bottom plug having an opening to allow air to pass through the bottom plug and the handle portion and into the area of the face portion.

6. The face shield according to claim 5, further comprising a hook connected to the bottom surface of the bottom plug to allow the face shield to be hung on a wall or other surface.

7. The face shield according to claim 5, additionally comprising a rim integrally formed along said top edge and directed inwardly toward the face of the user.

\* \* \* \* \*